United States Patent
Obara

(10) Patent No.: US 11,426,138 B2
(45) Date of Patent: Aug. 30, 2022

(54) RADIOGRAPHING APPARATUS, RADIOGRAPHING SYSTEM, AND DOSE INDEX MANAGEMENT METHOD

(71) Applicant: CANON KABUSHIKI KAISHA, Tokyo (JP)

(72) Inventor: Kazuma Obara, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 106 days.

(21) Appl. No.: 15/979,227

(22) Filed: May 14, 2018

(65) Prior Publication Data
US 2018/0333128 A1 Nov. 22, 2018

(30) Foreign Application Priority Data
May 19, 2017 (JP) .............................. JP2017-100189

(51) Int. Cl.
*A61B 6/00* (2006.01)

(52) U.S. Cl.
CPC ............ *A61B 6/542* (2013.01); *A61B 6/4291* (2013.01); *A61B 6/463* (2013.01); *A61B 6/465* (2013.01); *A61B 6/467* (2013.01); *A61B 6/545* (2013.01)

(58) Field of Classification Search
CPC . A61B 6/542; H05G 1/28; H05G 1/38; H05G 1/40; H05G 1/42; H05G 1/44; H05G 1/46
See application file for complete search history.

(56) References Cited

U.S. PATENT DOCUMENTS

| | | | | |
|---|---|---|---|---|
| 5,621,779 A | * | 4/1997 | Hughes | A61N 5/1048 378/65 |
| 6,292,534 B1 | * | 9/2001 | Linders | A61B 6/4233 348/E5.086 |
| 2009/0074143 A1 | * | 3/2009 | Tsukagoshi | A61B 6/542 378/97 |
| 2010/0002831 A1 | * | 1/2010 | Maack | A61B 6/06 378/16 |

(Continued)

FOREIGN PATENT DOCUMENTS

| | | | | |
|---|---|---|---|---|
| CN | 101506904 A | * | 8/2009 | ........... A61B 6/4405 |
| CN | 101506904 A | | 8/2009 | |

(Continued)

OTHER PUBLICATIONS

Translation of JP 2009268801 A (Year: 2009).*
Translation of CN 101506904 A (Year: 2006).*

*Primary Examiner* — David P Porta
*Assistant Examiner* — Mamadou Faye
(74) *Attorney, Agent, or Firm* — Canon U.S.A., Inc. IP Division

(57) ABSTRACT

A radiographing apparatus includes a selecting unit configured to select a target dose index for radiographing based on a radiographing imaging mode, a dose index acquiring unit configured to acquire a dose index from image data based on radiation transmitted through a subject, and a calculating unit configured to calculate a deviation index of the dose index with respect to the target dose index. Alternatively, the radiographing apparatus may include a display control unit configured to display, on a display unit, information regarding the imaging mode, the target dose index and the dose index.

16 Claims, 10 Drawing Sheets

(56) References Cited

U.S. PATENT DOCUMENTS

| | | | | |
|---|---|---|---|---|
| 2015/0036803 A1* | 2/2015 | Kuroki | ............... | A61B 6/463 378/98.5 |
| 2015/0100572 A1* | 4/2015 | Kalafut | ............... | G06Q 50/24 707/736 |
| 2016/0095567 A1* | 4/2016 | Tachikawa | ............ | A61B 6/542 378/98.2 |

FOREIGN PATENT DOCUMENTS

| | | | |
|---|---|---|---|
| JP | 2009-268801 A | | 11/2009 |
| JP | 2009268801 A | * | 11/2009 |
| JP | 2014-138654 A | | 7/2014 |
| JP | 2015-093013 A | | 5/2015 |
| JP | 2016-106953 A | | 6/2016 |
| WO | 2019/202695 A1 | | 10/2019 |

* cited by examiner

FIG. 7

[SERVICE TOOL/SYSTEM SETTINGS]

501 ☑ USE DOSE WARNING.

502 ○ REX  ● EI  ○ DI

GRID RADIOGRAPHY

503 ☑ UPPER LIMIT VALUE: [＿＿＿＿] 507
504 ☑ LOWER LIMIT VALUE: [＿＿＿＿] 508

GRIDLESS RADIOGRAPHY

505 ☑ UPPER LIMIT VALUE: [＿＿＿＿] 509
506 ☑ LOWER LIMIT VALUE: [＿＿＿＿] 510

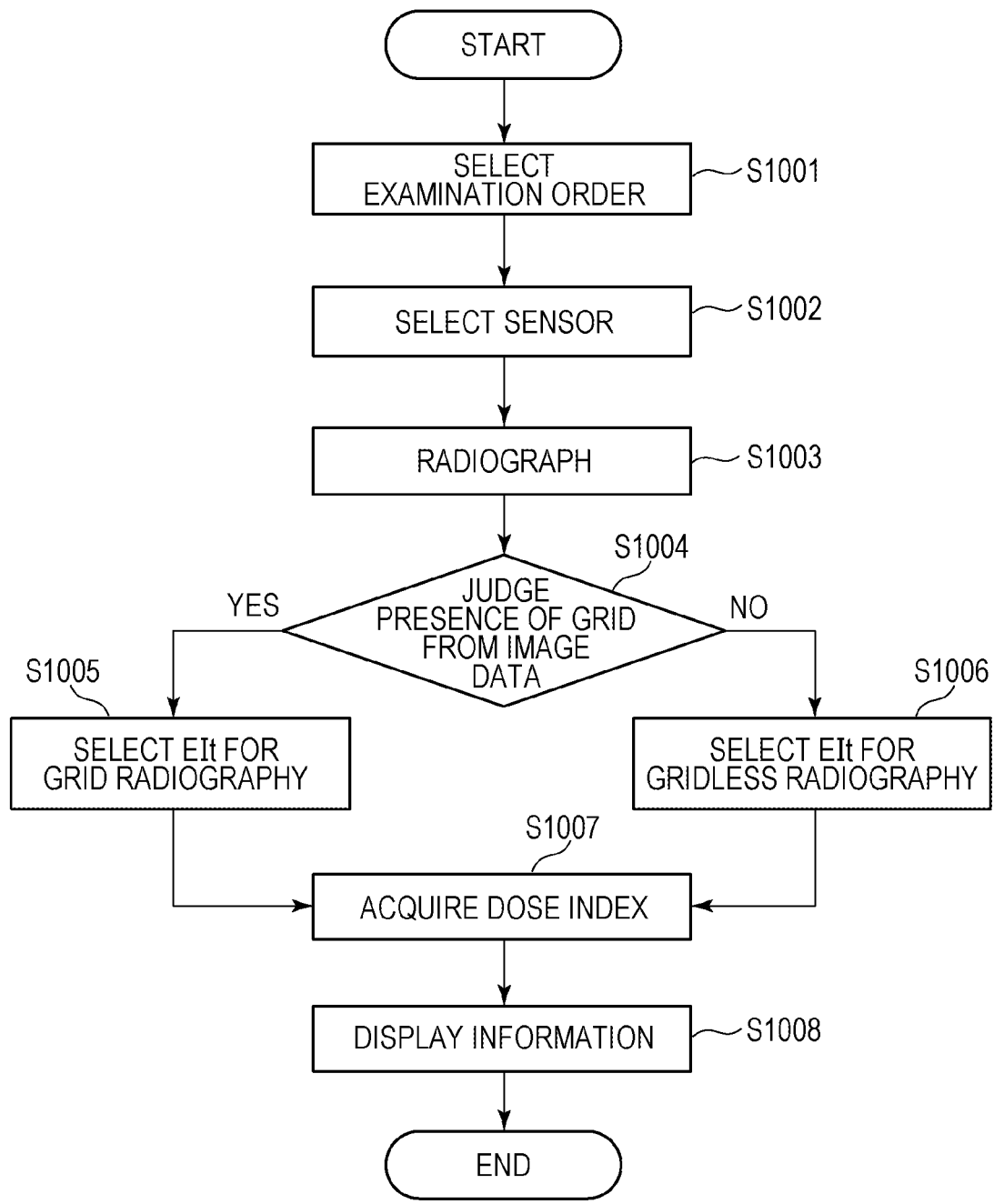

RADIOGRAPHING APPARATUS, RADIOGRAPHING SYSTEM, AND DOSE INDEX MANAGEMENT METHOD

BACKGROUND OF THE INVENTION

Field of the Invention

The present disclosure relates to a radiographing apparatus for radiographing, a radiographing system, and a dose index management method.

Description of the Related Art

In recent years, a radiographing system has been widely spread in which radiation is irradiated from radiation generating apparatus to a radiographing apparatus, and in which the radiographing apparatus generates a radiographic image so that the radiographic image can be displayed.

Such a radiographing apparatus can calculate a dose index corresponding to a dose based on a representative pixel value acquired from the radiographic image. Japanese Patent Laid-Open No. 2009-268801 discloses a radiographing apparatus in which a target dose index is set for each subject region to be radiographed so that an operator can evaluate whether the dose for radiographing has been appropriate or not based on the actually calculated dose index and the target dose index.

In radiographing by a radiographing apparatus having a grid attached thereto, the grid absorbs scattered rays of the radiation and a part of the radiation. Thus, the dose index calculated from the radiographic image can be lower than that of a case without the grid even with an equal dose of radiation generated by the radiation generating apparatus. In other words, the dose index calculated from a radiographic image depends on the imaging mode used for radiographing (such as the presence or absence of the grid). Japanese Patent Laid-Open No. 2009-268801 does not mention about selection of a target dose index in consideration of the imaging mode used in radiographing.

SUMMARY OF THE INVENTION

The present disclosure provides a radiographing apparatus, a radiographing system, and a dose index management method which can select a target dose index suitable for a radiographing imaging mode and appropriately evaluate a dose index. A radiographing apparatus according to an aspect of the present disclosure includes a selecting unit configured to select a target dose index for radiographing based on a radiographing imaging mode, a dose index acquiring unit configured to acquire a dose index from image data based on radiation transmitted through a subject, and a calculating unit configured to calculate a deviation index of the dose index with respect to the target dose index. Alternatively, the radiographing apparatus may include a display control unit configured to display on a display unit information regarding the imaging mode, the target dose index and the dose index.

Further features of the present invention will become apparent from the following description of exemplary embodiments with reference to the attached drawings.

BRIEF DESCRIPTION OF THE DRAWINGS

FIG. 7 illustrates an example of a screen display for setting an allowable range for a dose warning function according to the present disclosure.

FIG. 10 is a flowchart illustrating operations according to a third embodiment of the present disclosure.

DESCRIPTION OF THE EMBODIMENTS

Embodiments of the present disclosure will be described below with reference to the attached drawings. Each of the embodiments of the present invention described below can be implemented solely or as a combination of a plurality of the embodiments or features thereof where necessary or where the combination of elements or features from individual embodiments in a single embodiment is beneficial.

First Embodiment

Figure 1:
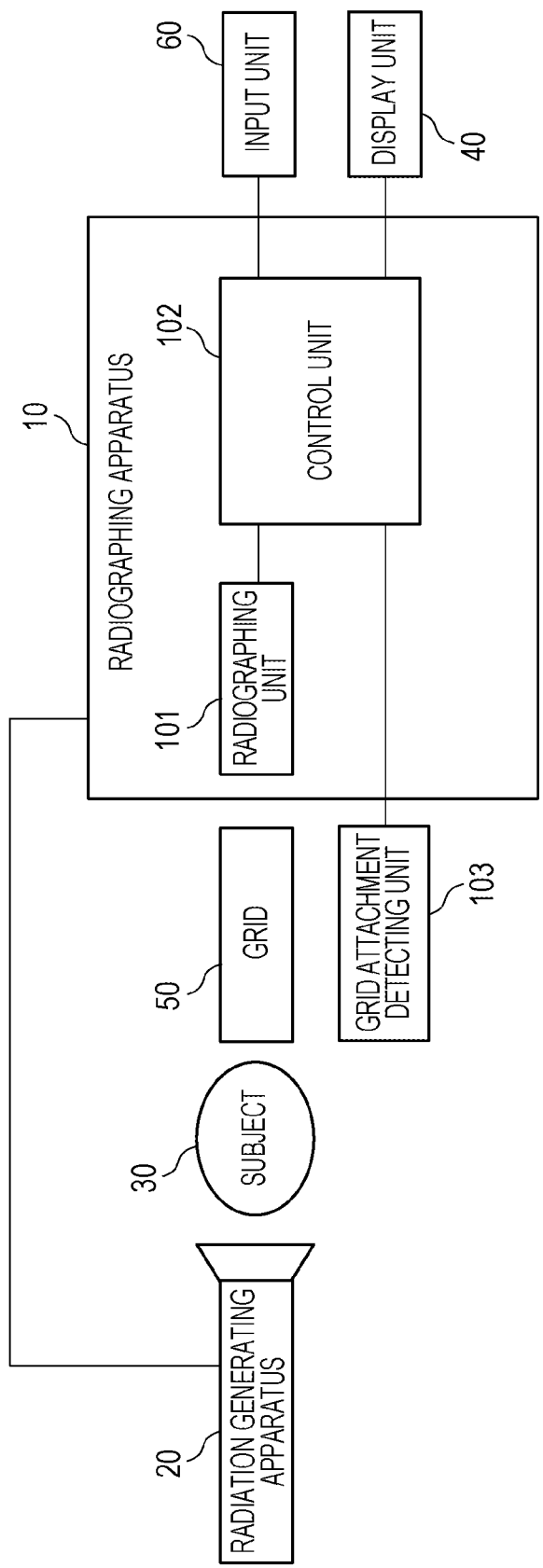
FIG. 1 is a block diagram illustrating an example of a configuration of a radiographing system according to the present disclosure.

FIG. 1 illustrates a configuration example of a radiographing system according to the present disclosure. The radiographing system includes a radiation generating apparatus 20 configured to generate radiation, radiographing apparatus 10 configured to image the radiation, a display unit 40 configured to display a radiographic image based on the radiation imaged by the radiographing apparatus 10, and an input unit 60 configured to be usable by an operator to input information. The input unit 60 may be a keyboard, buttons, or a touch panel and may be usable by an operator to input information.

The radiation generating apparatus 20 has a function for generating radiation. The radiation generating apparatus 20 is configured to irradiate radiation to a predetermined irradiation range. The radiation generating apparatus 20 is installed on a floor surface or a ceiling through a supporting member (not illustrated). The radiation generating apparatus 20 has a diaphragm (not illustrated) on its irradiation surface, and the diaphragm is configured to shield radiation. An operator may control the diaphragm configured to shield radiation to set an irradiation range for radiation irradiated from the radiation generating apparatus 20.

The radiographing apparatus 10 includes a radiographing unit 101 and a control unit 102. The radiographing unit 101 is configured to detect radiation transmitted through a subject 30 and thus generate image data. The control unit 102 is configured to process the image data and output the radiographic image to the display unit 40.

The radiographing unit 101 is configured to detect the radiation transmitted through the subject 30, convert it to an electric signal, and generate image data therefrom. The radiographing unit 101 detects the radiation transmitted through the subject 30 as electric charges corresponding to the dose of the transmitted radiation. For example, the radiographing unit 101 may be a direct conversion type sensor configured to convert radiation directly to electric charges, such as an a-Se (amorphous selenium) sensor configured to convert radiation to electric charges, or an indirect type sensor applying a scintillator such as a CsI (cesium iodide), and a photoelectric converting element such as an a-Si (amorphous silicon). The radiographing unit 101 may perform A/D conversion on the detected electric charges to generate image data. The radiographing unit 101 may output the image data to the control unit 102.

The control unit 102 has components for control such as a CPU and a memory. The CPU may be a microprocessor and is configured to perform arithmetic operations for radiographing processing, image processing, and display control processing and logical judgment to control devices under control of the control unit 102. The memory is a computer readable/writable random access memory and, as a main memory, is configured to temporally store data received from a device. The control unit 102 is configured by installing software programs in a personal computer, but the control unit 102 may be configured by a dedicated hardware unit. While the radiographing unit 101 and the control unit 102 are provided separately in the radiographing apparatus 10, they are not necessarily to be provided separately. A part of the functionality of the control unit 102 may be contained in the radiographing unit 101.

The control unit 102 can control the radiographing unit 101 for performing radiographing. The control unit 102 performs processing such as image processing on image data and outputs the processed image data as a radiographic image to the display unit 40. The control unit 102 can control the display unit 40 to set a display form for the radiographic image.

The display unit 40 may be a liquid crystal display or a CRT and is configured to display a radiographic image output from the radiographing apparatus 10 and information input from the input unit 60.

A grid 50 is to be attached (placed) to the radiographing apparatus 10. The grid 50 has a function of shielding scattered rays based on the radiation. The grid 50 includes a plurality of metallic foils and is configured to absorb scattered rays from the subject 30 and a part of the radiation generated by the radiation generating apparatus 10 transmitted through the subject 30.

The grid 50 is attached so as to cover the radiographing unit 101 in the radiographing apparatus 10 in accordance with a region for imaging the subject 30. For example, in a case where the abdomen of the subject 30 is a region for imaging, the grid 50 is attached to the radiographing apparatus 10. In a case where the limbs of the subject 30 are a region for imaging, the grid 50 may not be attached to the radiographing apparatus 10 because of the weaker scattered rays therefrom.

The radiographing system includes a grid attachment detecting unit 103 configured to detect an attachment state of the grid 50. The grid attachment detecting unit 103 may be installed within a holding unit configured to hold the radiographing apparatus 10 or may be installed within the radiographing apparatus 10. The grid attachment detecting unit 103 is configured to detect whether the grid 50 is attached to the radiographing apparatus 10 or not. The attachment of the grid 50 may be physically detected by a contact sensor, a magnetic sensor, a pressure sensor or the like.

Figure 2:
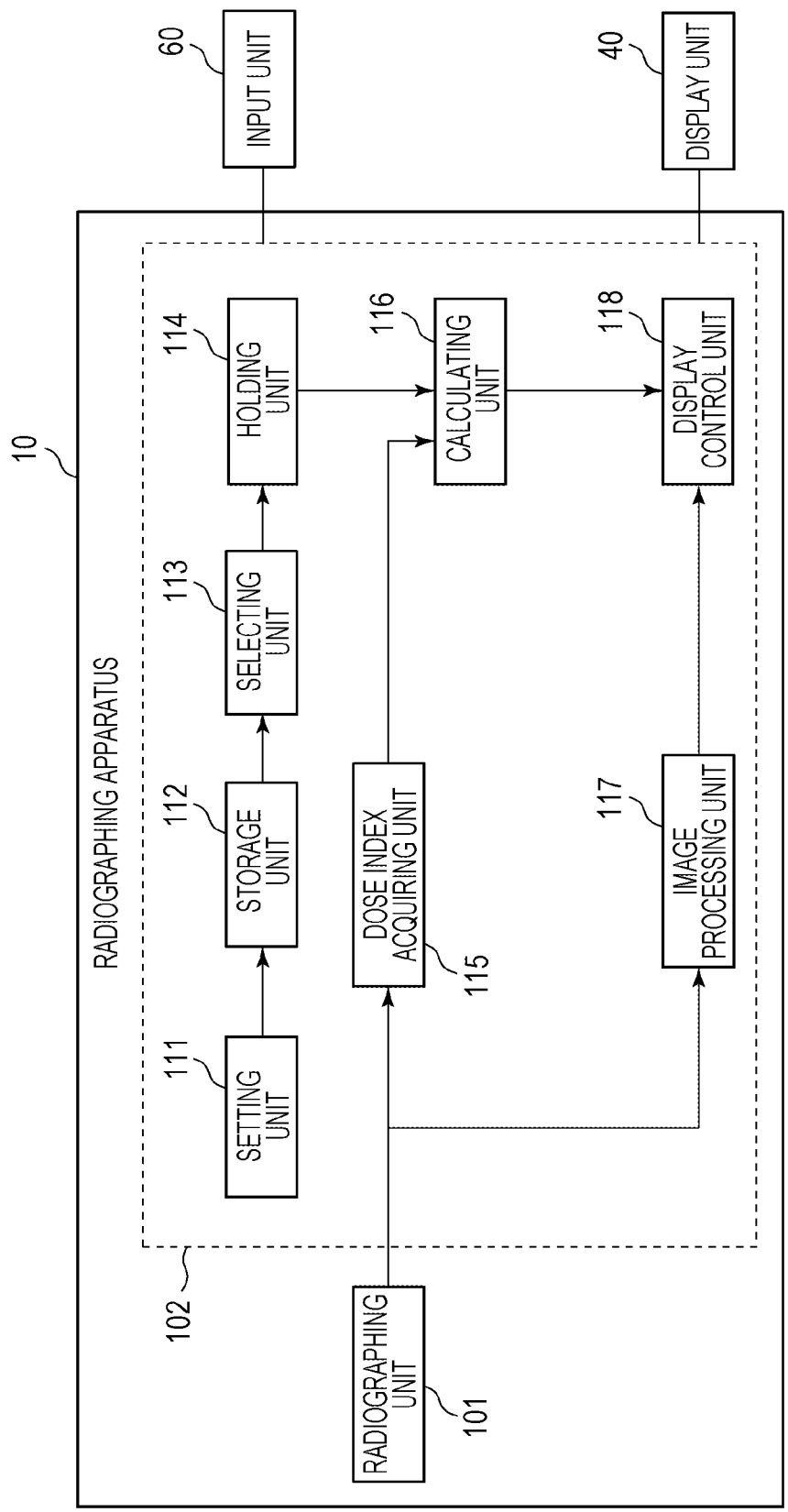
FIG. 2 is a block diagram illustrating another example of the configuration of the radiographing apparatus according to the present disclosure.

FIG. 2 illustrates a configuration of the radiographing apparatus 10 in the radiographing system according to an embodiment of the present disclosure. The radiographing apparatus 10 includes a setting unit 111 configured to set a target dose index and a storage unit 112 configured to store a plurality of target dose indices set by the setting unit 111.

The radiographing apparatus 10 further includes a selecting unit 113 and a holding unit 114. The selecting unit 113 is configured to select a target dose index from a plurality of target dose indices stored in the storage unit 112. The holding unit 114 is configured to hold the selected target dose index. The radiographing apparatus 10 further includes a dose index acquiring unit 115 and a calculating unit 116. The dose index acquiring unit 115 is configured to acquire a dose index from image data based on the radiation transmitted through the subject 30. The calculating unit 116 is configured to calculate a deviation index of a dose index with respect to a target dose index.

The radiographing apparatus 10 further includes an image processing unit 117 and a display control unit 118. The image processing unit 117 is configured to process image data output from the radiographing unit 101 to generate a radiographic image. The display control unit 118 is configured to display on the display unit 40 the radiographic image and a deviation index of a dose index with respect to a target dose index.

The dose index acquiring unit 115 is configured to acquire a dose index from image data output from the radiographing unit 101. The dose index may be an Exposure Index (EI), for example. The dose index is a value for evaluating a dose used for radiographing. The term "EI" refers to an index standardized as IEC62494-1 in international Electric Conference: IEC.

More specifically, the dose index acquiring unit 115 may first set a predetermined region of interest in image data output from the radiographing unit 101 and calculates a representative pixel value in the region of interest. The representative pixel value may be a pixel value being an average value, a median value or a mode, for example. The dose index acquiring unit 115 may convert the representative pixel value to a dose based on a relationship between known incident dose and pixel value. The dose index acquiring unit 115 then may multiply the converted dose by a constant to calculate a dose index (EI). The dose index acquiring unit 115 calculates an EI as a dose index, but the dose index may only be required for determining whether the dose having reached the radiographing unit 101 is relatively large or small and may be a dose index excluding an EI. The dose index acquired by the dose index acquiring unit 115 may be output to the calculating unit 116.

Figure 3:
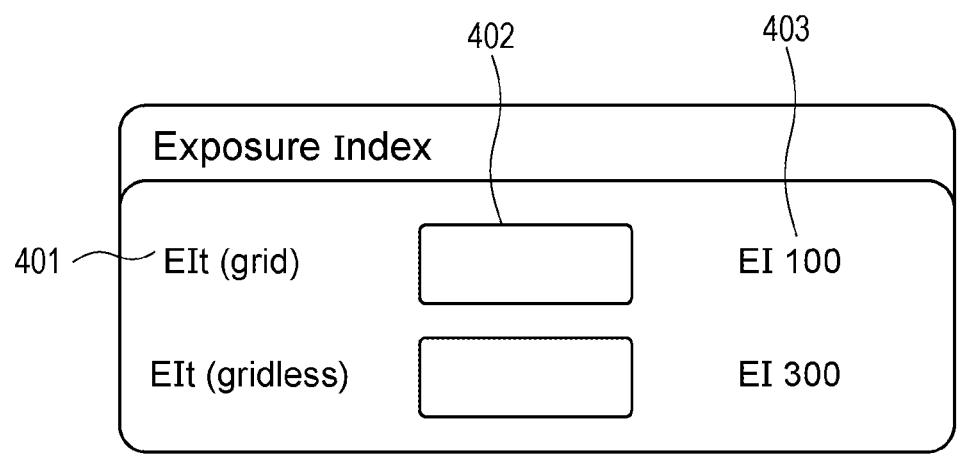
FIG. 3 illustrates an example of a screen on a display unit for setting a target dose index according to the present disclosure.

Next, the setting unit 111 configured to set a target dose index will be described with reference to FIG. 3. FIG. 3 illustrates an example of a screen to be displayed on the display unit 40 for setting a plurality of different target dose indices in the setting unit 111. The setting screen for setting a target dose index is displayed on the display unit 40. Here, the setting screen displays a target dose index name 401, a target dose index input field 402, and a dose index reference value 403. A target dose index (set value) in the target dose index input field 402 is to be input through the input unit 60. Here, an Exposure Index Target (EIt) is set as a target dose index. An EIt is an index standardized as IEC62494-1.

As a target dose index name 401, at least one target dose index name to be associated with an examination order of the subject 30 is displayed. The target dose index name may be associated with a region for imaging (such as the abdomen or the limb) of the subject 30. For example, in a case where the abdomen of the subject 30 is a region for imaging, a target dose index name may be set for indicating that the grid 50 is to be attached to the radiographing apparatus 10. In a case where the limb of the subject 30 is a region for imaging, a target dose index name may be set for indicating that the grid 50 is not to be attached to the radiographing apparatus 10.

Here, the name of the target dose index EIt (grid) assuming that the grid 50 is to be attached to the radiographing apparatus 10 is displayed as the target dose index name 401. A name of the target dose index EIt(gridless) assuming a case where the grid 50 is not to be attached to the radiographing apparatus 10 is displayed as the target dose index name 401.

The target dose index input field 402 accepts input of at least one target dose index. An operator can input a target dose index EIt through the input unit 60. More specifically, an operator can input a target dose index EIt(grid) assuming a case where the grid 50 is to be attached to the radiographing apparatus 10 through the input unit 60. An operator can input a target dose index EIt(gridless) assuming a case where the grid 50 is attached to the radiographing apparatus 10 through the input unit 60.

The dose index reference value 403 corresponds to a dose index EI calculated from a radiographic image captured in the past. The dose index reference value 403 is a reference value to be referred by an operator for setting a target dose index in the target dose index input field 402. For example, the dose index reference value 403 corresponds to a statistic (such as an average value) in a plurality of dose indices calculated from a plurality of radiographic images captured in the past in a case where the EI grid 50 is to be attached to the radiographing apparatus 10 and in a case where the EI grid 50 is not to be attached to the radiographing apparatus 10.

The dose index reference value 403 corresponding to the target dose index EIt(grid) is a dose index EI calculated from a radiographic image captured in the past with the grid 50 attached to the radiographing apparatus 10. The dose index reference value 403 corresponding to the target dose index EIt(gridless) is a dose index EI calculated from a radiographic image captured in the past with the grid 50 not attached to the radiographing apparatus 10.

All information on a screen for setting target dose indices illustrated in FIG. 3 is not necessarily displayed, but at least the target dose index name 401 and the target dose index input field 402 may only be displayed.

The storage unit 112 is configured to store a plurality of target dose indices set on the setting screen for setting target dose indices illustrated in FIG. 3. The storage unit 112 distinguishes and stores a target dose index EIt(grid) assuming a case where the grid 50 is attached to the radiographing apparatus 10 and a target dose index EIt(gridless) assuming a case where the grid 50 is not attached to the radiographing apparatus 10. The storage unit 112 can store a target dose index EIt(grid) and a target dose index EIt(gridless) as a first target dose index and a second target dose index, respectively.

The selecting unit 113 selects a target dose index for radiography based on a radiographing imaging mode (e.g. an imaging mode used for/in the radiographing). The imaging mode may be an attachment state of the grid 50, for example. In a case where the grid 50 is to be attached to the radiographing apparatus 10, the selecting unit 113 selects the target dose index EIt(grid). In a case where the grid 50 is not to be attached to the radiographing apparatus 10, the selecting unit 113 selects the target dose index EIt(gridless).

The holding unit 114 is configured to hold the target dose index selected by the selecting unit 113. The target dose index held in the holding unit 114 corresponds to a dose index acquired from image data output from the radiographing unit 101. In other words, the target dose index held in the holding unit 114 and the dose index acquired in the dose index acquiring unit 115 are based on image data captured in the same imaging mode (attachment state of the grid).

The calculating unit 116 is configured to calculate a deviation index of the dose index EI with respect to the target dose index EIt based on the dose index EI output from the dose index acquiring unit 115 and the target dose index EIt output from the holding unit 114 (selecting unit 113).

A deviation index (DI) is an index standardized as IEC62494-1. More specifically, the deviation index DI can be calculated by the following expression:

$$DI = 10 \log_{10}(EI/EIt)$$

It is generally regarded that a deviation index DI higher than 0 results in a dose higher than a normal dose and that a deviation index DI lower than 0 results in a dose lower than the normal dose. The deviation index DI calculated by the calculating unit 116 is output to the display control unit 118.

The image processing unit 117 has a function for performing image processes such as a noise reduction and a gradation process on image data output from the radiographing unit 101. The image processing unit 117 can further perform image processes such as cropping and rotating on image data output from the radiographing unit 101. The image data image-processed by the image processing unit 117 is output to the display control unit 118 as a radiographic image.

The display control unit 118 is configured to cause the display unit 40 to display the radiographic image. The display control unit 118 may cause the display unit 40 to display information regarding a radiographing imaging mode as well as a deviation index of a dose index with respect to a target dose index. The display control unit 118 may cause the display unit 40 to display information on a radiographing imaging mode as well as a target dose index and a dose index.

Figure 4:
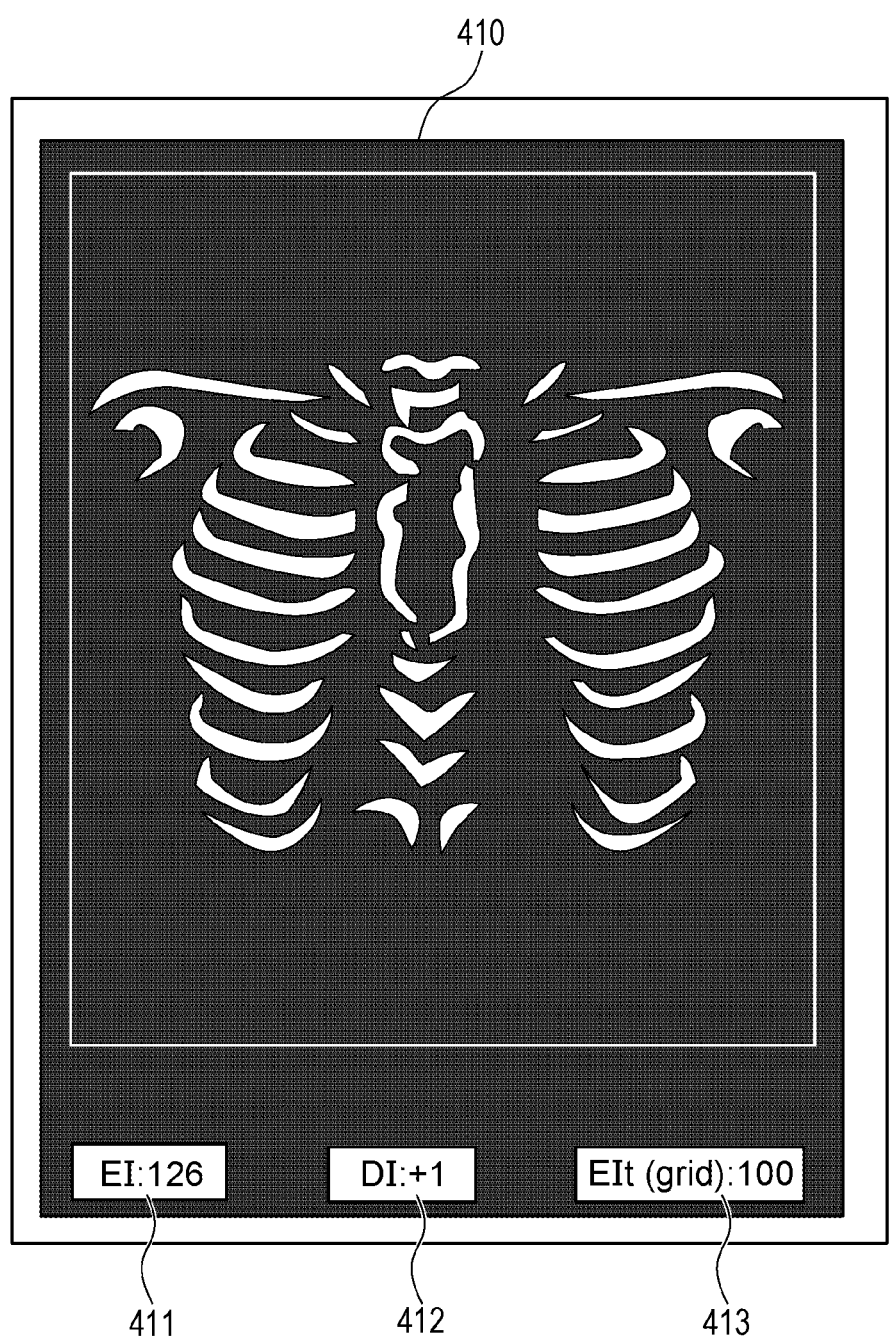
FIG. 4 illustrates another example of a screen on the display unit which displays a radiographic image according to the present disclosure.

A specific display form of the display unit 40 will be described with reference to FIG. 4. As illustrated in FIG. 4, the display unit 40 may display a radiographic image 410 image processed by the image processing unit 117. A dose index 411 acquired by the dose index acquiring unit 115 is displayed in a region neighboring to the radiographic image 410 on the display unit 40. A deviation index 412 of the dose index with respect to a target dose index 413, which is calculated by the calculating unit 116, and the target dose index 413 selected by the selecting unit 113 are displayed on the display unit 40.

The target dose index 413 displayed on the display unit 40 includes information indicating the attachment state of the grid 50. EIt(grid) indicates that the grid 50 is attached to the radiographing apparatus 10. EIt(gridless) indicates that the grid 50 is not attached to the radiographing apparatus 10. From the information indicating the attachment state of grid 50, an operator can recognize the target dose index EIt indicating that the grid 50 is attached or the target dose index EIt indicating that the grid 50 is not attached. The display unit 40, irrespective of the attachment state of the grid 50, may display all of target dose indices stored in the storage unit 112 or may display a target dose index held in the holding unit 114. All of these pieces of information may not necessarily be displayed, but an operator may individually define items to be displayed.

Referring to FIG. 4, in a case where the dose index 411 acquired by the dose index acquiring unit 115 is "126" and the target dose index 413 selected by the selecting unit 113 is "100", the deviation index 412 of the dose index with respect to the target dose index, which is calculated based on the number "1", is "+1". An operator can recognize that the dose is higher than a normal dose because the deviation index DI is higher than 0. Thus, the operator can recognize that the deviation index 412 has been calculated when the grid 50 is attached to the radiographing apparatus 10.

According to the present disclosure, the display unit 40 may display at least the radiographic image 410, the dose index 411, and the deviation index 412 or the target dose index 413 on one screen. An operator may recognize based on the deviation index 412 whether the dose reaching the radiographing unit 101 is relatively high or low. An operator can recognize how much the dose index 412 is higher or lower than the target dose index 413.

Here, operations to be performed in the radiographing system according to the present disclosure will be described with reference to a flowchart illustrated in FIG. 5.

In step S501, an operator selects an examination order for which a region for imaging of the subject 30 is set.

In step S502, the operator may select the radiographing apparatus 10 (sensor) to be used for imaging. A case where the radiographing apparatus 10 does not have a grid detection function for detecting the grid 50 and a case where use of the grid 50 cannot be physically judged will be described with reference to other embodiments.

In step S503, the grid attachment detecting unit 103 judges whether the grid 50 is attached. The grid attachment detecting unit 103 may physically detect the attachment of the grid 50 by using an external measure such as a change of the weight of the radiographing apparatus 10 due to the attachment or information regarding a camera provided in the radiographing system. The grid attachment detecting unit 103 is not always required, but an operator can manually input through the input unit 60 that the grid 50 is attached. The information on the attachment of the grid 50 input through the input unit 60 is output to the control unit 102.

If the grid 50 is attached to the radiographing apparatus 10, the processing moves to step S504. If the grid 50 is not attached to the radiographing apparatus 10, the processing moves to step S505.

In step S504, the selecting unit 113 selects a target dose index for a case where the grid 50 is attached to the radiographing apparatus 10 from at least one target dose index stored in the storage unit 112. The target dose index selected by the selecting unit 113 is held in the holding unit 114.

In step S505, the selecting unit 113 selects a target dose index for a case where the grid 50 is not attached to the radiographing apparatus 10 from at least one target dose index stored in the storage unit 112. The target dose index selected by the selecting unit 113 is held in the holding unit 114.

In step S506, an operator performs radiographing. The radiographing unit 101 detects the radiation transmitted through the subject 30, converts it to an electric signal, and outputs resulting image data.

In step S507, the dose index acquiring unit 115 acquires a dose index from the image data.

In step S508, the display unit 40 displays the dose index. The display unit 40 displays the dose index, the deviation index or the target dose index as well as information regarding a radiographing imaging mode on one screen. An operator can check the dose index for the current radiographing is within an allowable range.

The radiographing system (or the radiographing apparatus) according to this embodiment includes the selecting unit 113 configured to select a target dose index for radiographing based on a radiographing imaging mode (or the presence or absence of the grid), the dose index acquiring unit 115 configured to acquire a dose index image data based on the radiation transmitted through a subject, and the calculating unit 116 configured to calculate a deviation index of the dose index with respect to the target dose index selected by the selecting unit 113. Alternatively, the radiographing system (or the radiographing apparatus) may include the display control unit 118 configured to display the target dose index selected by the selecting unit 113 and the dose index as well as information regarding the imaging mode. Thus, an operator can select a target dose index suitable for the imaging mode and can appropriately evaluate a dose index.

Second Embodiment

A second embodiment will be described with reference to FIG. 6 to FIG. 8. The second embodiment is different from the first embodiment in that it further includes a judging unit 120 configured to judge whether a dose index is within a predefined allowable range or not.

Figure 6:
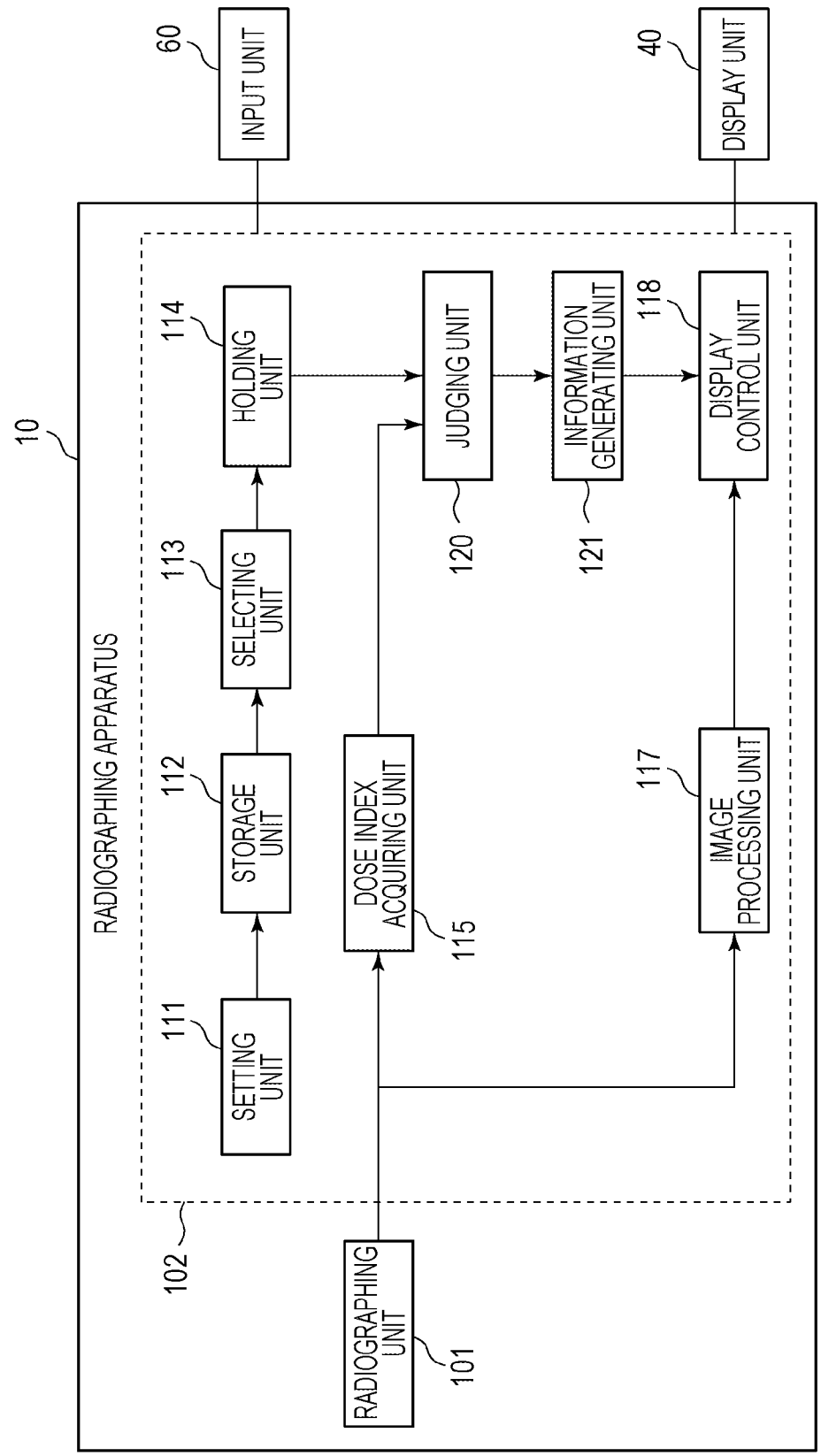
FIG. 6 is a block diagram illustrating a configuration example of the radiographing apparatus according to the present disclosure.

FIG. 6 illustrates a configuration of the radiographing apparatus 10 according to the present disclosure. Because the second embodiment has the same configuration as that illustrated in FIG. 2 except for the judging unit 120 and an information generating unit 121, any repetitive descriptions excluding descriptions regarding the judging unit 120 and the information generating unit 121 will be omitted.

The judging unit 120 is configured to use a dose index acquired by the dose index acquiring unit 115 and a target dose index held in the holding unit 114 to judge whether the dose index is within a predefined allowable range or not.

If the judging unit 120 judges that the dose index is not within the allowable range (or out of the allowable range), the information generating unit 121 generates warning information. The information generating unit 121 generates warning information if the judging unit 120 judges that the dose index is not in the allowable range.

The display control unit 120 is configured to generate a screen to be presented to an operator based on a radiographic image output from the image processing unit 119 and warning information generated by the information generating unit 121, and controls the display state of the screen to be displayed on the display unit 40.

FIG. 7 is an example of a screen to be displayed for setting an upper limit value and a lower limit value within an allowable range for a dose warning function. If the judging unit 120 judges that the dose index of the currently captured image data is out of an appropriate dose range, the dose warning function warns an operator of it. More specifically, a check box area 501 is displayed for the dose warning function to be checked to enable the dose warning function. Referring to FIG. 7, the check box area 501 is checked, which means that the dose warning function is enabled.

When the dose warning function is enabled, an index selection button 502 for selecting which index is to be used to use the dose warning function is displayed. According to this embodiment, one of a sensitivity index REX, a dose index EI, and a deviation index DI is selectable.

The setting screen includes check box areas 503 to 506 for dose judgment reference values to be checked for enabling a set upper limit value or lower limit value for determining whether a dose index is within the allowable range, and dose judgment reference value input fields 507 to 510 accepting input of an upper limit value or a lower limit value for determining that the dose index is within the allowable range. All of these pieces of information are not necessarily required to be displayed, at least one of the dose judgment reference value check box areas 503 to 506 and at least one of the dose judgment reference value input fields 507 to 510 may only be provided.

The upper limit values and the lower limit values defining an allowable range for the set target dose index and a dose warning function are stored in the judging unit 120. The judging unit 120 is configured to use the target dose index to judge whether the dose index of the current radiograph is within the allowable range. More specifically, the judging unit 120 may compare the upper limit value of the allowable range for the target dose index and the dose index of the current radiograph to judge whether the current dose index is higher. The judging unit 120 is further configured to compare the lower limit value of the allowable range for the target dose index and the dose index of the current radiograph to judge whether the current dose index is lower. If it is judged that the dose index is out of the allowable range, the information generating unit 121 generates warning information.

Figure 8:
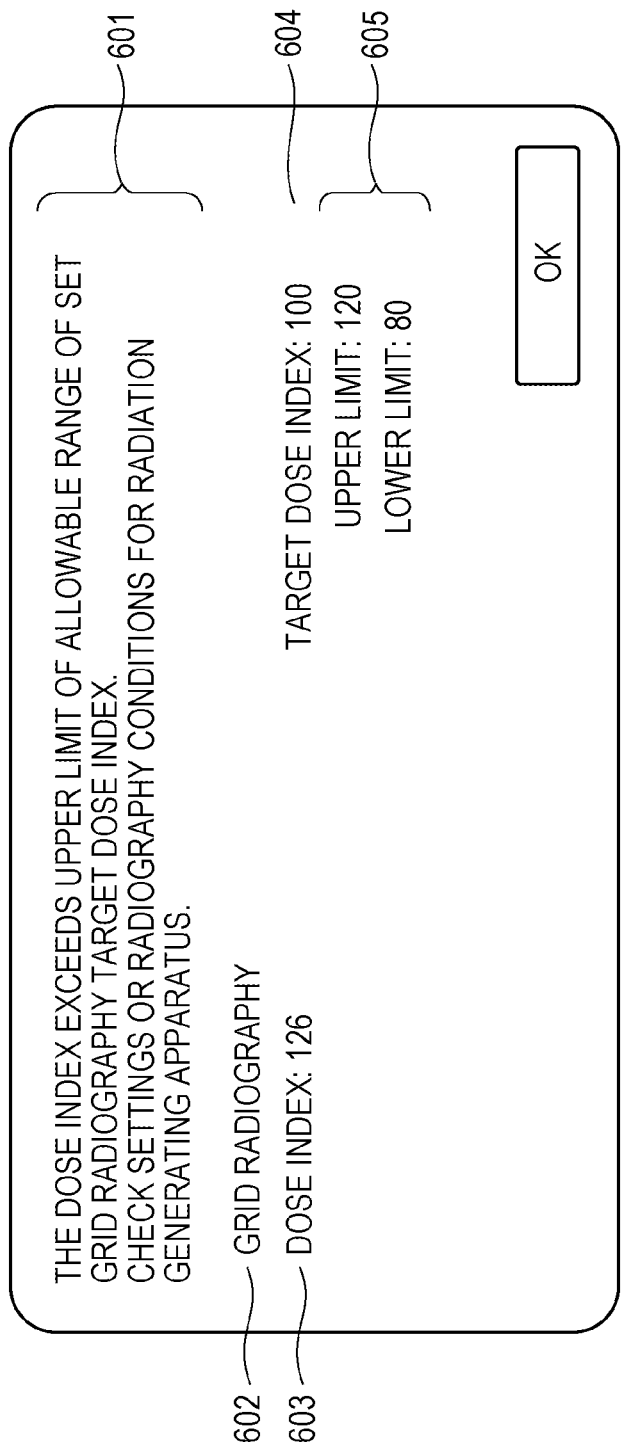
FIG. 8 illustrates an example of a screen on the display unit displaying warning information according to the present disclosure.

FIG. 8 illustrates an example of a display area for warning information generated by the information generating unit 121. More specifically, the display area displays warning information 601, a imaging mode 602 for the target dose index corresponding to the selected examination order, and a dose index 603 acquired by the dose index acquiring unit 115 for the current radiographing. The display area further displays a target dose index 604 held in the holding unit 114 and information 605 regarding an allowable range set in the dose judgment reference value input fields 507 to 510. The warning information 601 is displayed such as "The dose index exceeds the upper limit of allowable range of set grid radiography target dose index. Check settings or radiography conditions for radiation generating apparatus." The display control unit 120 is configured to control the display state of the screen to be displayed on the display unit 40 for presenting a radiographic image image-processed by the image processing unit 117, warning information generated by the information generating unit 121 or a screen displaying a dose index and a target dose index.

All of these pieces of information are not necessarily displayed, but at least information including the warning information 601 and the imaging mode 602 may only be displayed. The information generating unit 121 does not generate warning information in a case where the dose index acquired by the dose index acquiring unit 115 in the current radiographing is within the allowable range.

The judging unit 120 judges whether the deviation index of the dose index is within a predefined allowable range or not. If the judging unit 120 judges that the dose index is not within the allowable range (or out of the allowable range), the information generating unit 121 generates warning information.

The radiographing system (or the radiographing apparatus) according to this embodiment judges whether the dose index (deviation index) is within a predefined allowable range or not and notifies an operator of warning information.

Thus, the operator can set a dose suitable for radiography for the radiation generation unit 20.

Third Embodiment

A third embodiment will be described with reference to FIGS. 9 and 10. The third embodiment is different from the first and second embodiments in that a grid attachment judging unit 130 is further provided which is configured to analyze image data output from the radiographing unit 101 and determine the attachment state of the grid 50 and that the selecting unit 113 is further configured to select a target dose index based on the grid attachment state.

Figure 9:
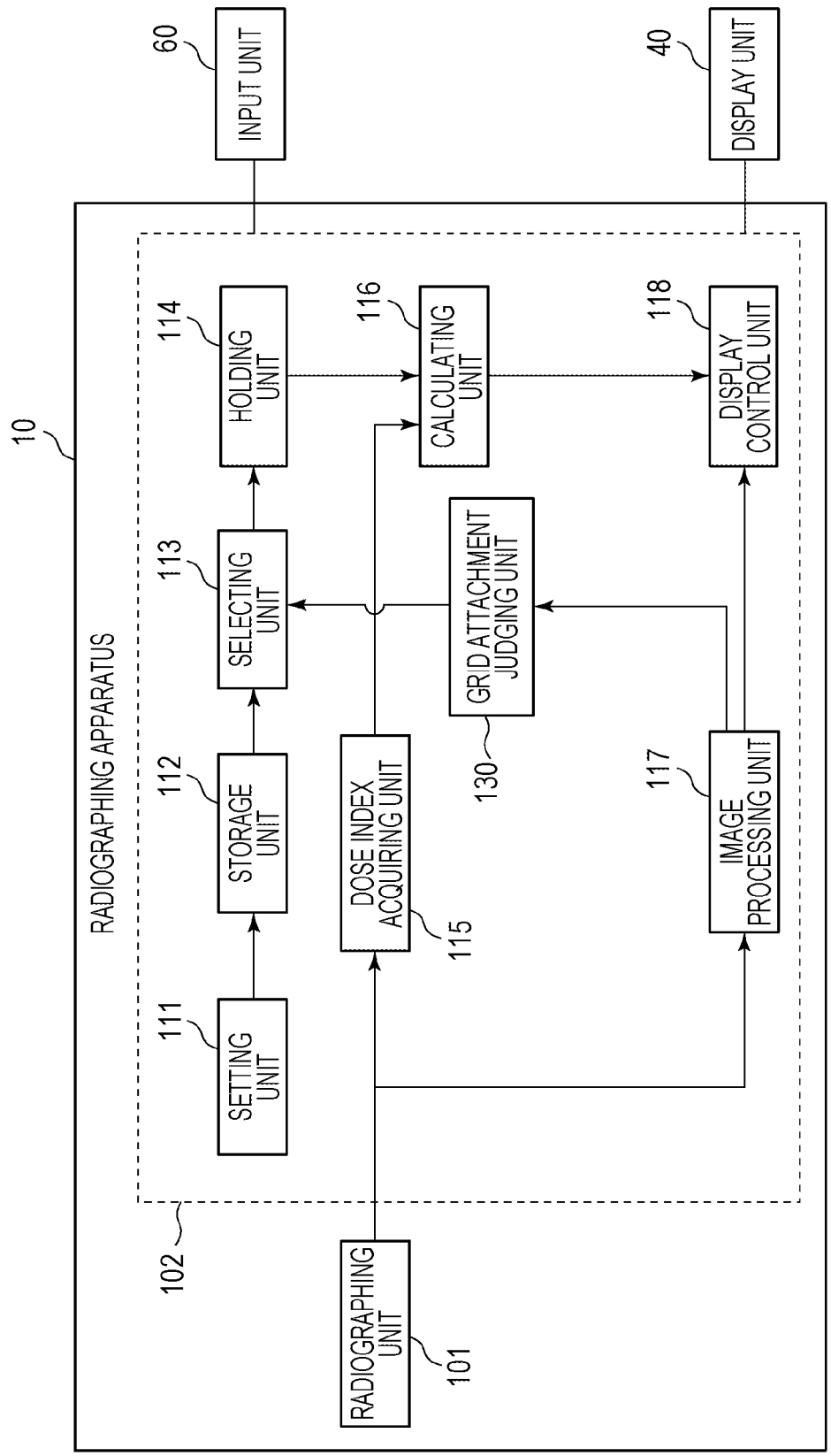
FIG. 9 is a block diagram illustrating another configuration example of the radiographing apparatus according to the present disclosure.

FIG. 9 illustrates a configuration of the radiographing apparatus 10 according to the present disclosure. Because the third embodiment has the same configuration as that illustrated in FIG. 2 except for the grid attachment judging unit 130, any repetitive descriptions excluding descriptions regarding the grid attachment judging unit 130 will be omitted.

The image processing unit 117 is configured to perform image processes on image data output from the radiographing unit 101 and output the result to the grid attachment judging unit 130. The grid attachment judging unit 130 is configured to judge based on the image data whether the grid 50 is attached for the radiographing or not. More specifically, the grid attachment judging unit 130 detects the presence or absence of a grid pattern being a striped pattern generated by the grid 50 in the image data. More specifically, the grid attachment judging unit 130 judges whether a certain frequency component in a frequency spectrum of frequency-analyzed image data has a peak or not. If the frequency spectrum has a peak, the grid attachment judging unit 130 judges that the grid 50 is attached. If not, the attachment judging unit 130 judges that the grid 50 is not attached.

The grid attachment judging unit 130 outputs the attachment state of the grid 50 acquired by analyzing the image data to the selecting unit 113. The selecting unit 113 is configured to select a target dose index for radiographing based on the attachment state of the grid 50. Thus, if the grid 50 is attached to the radiographing apparatus 10, the selecting unit 113 selects a target dose index EIt(grid). If the grid 50 is not attached to the radiographing apparatus 10, the selecting unit 113 selects a target dose index EIt(gridless).

Next, operations to be performed in the radiographing system according to the present disclosure will be described with reference to a flowchart illustrated in FIG. 10.

Figure 5:
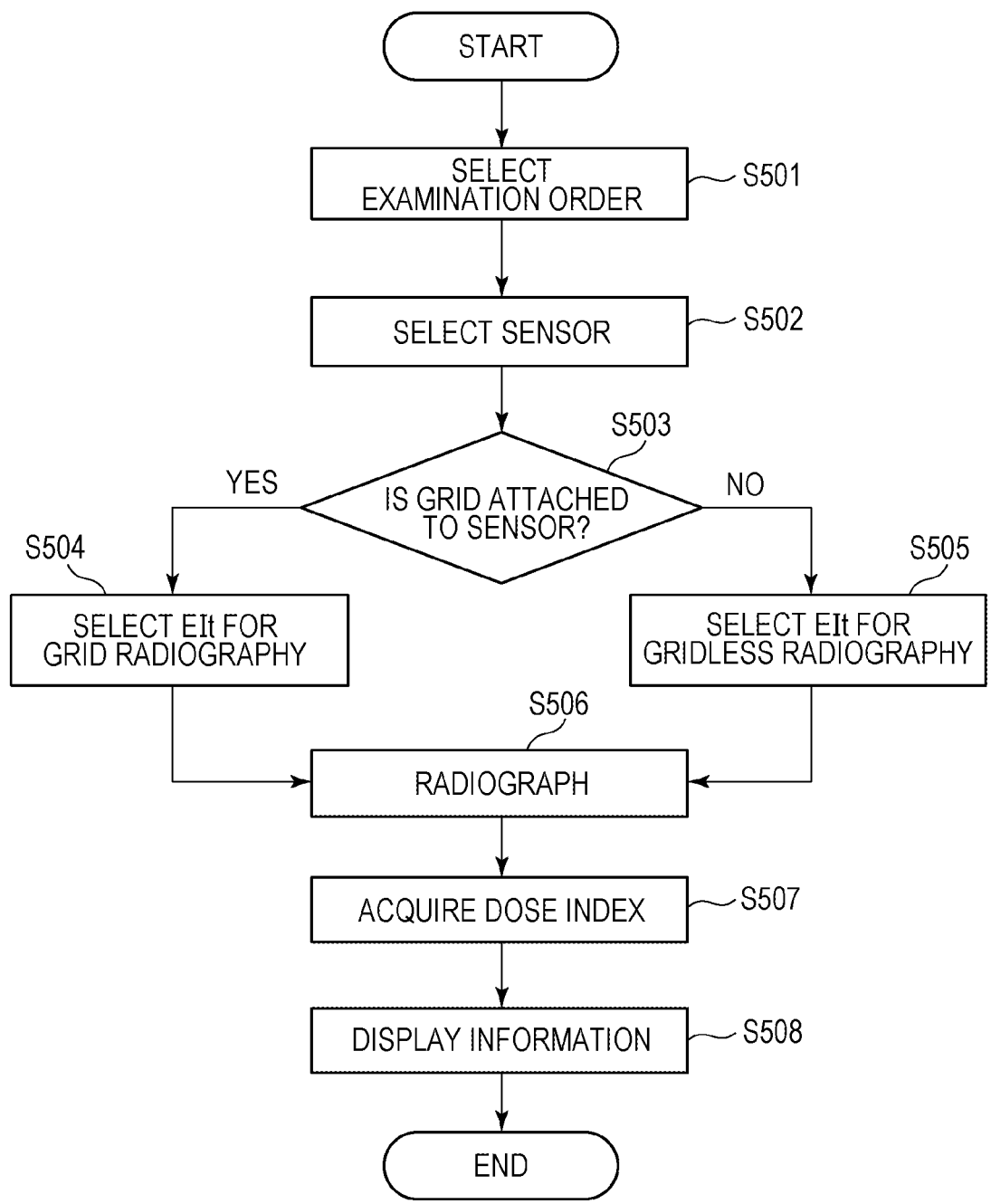
FIG. 5 is a flowchart illustrating operations according to a first embodiment of the present disclosure.

Because the processing to be performed in each of step S1001 to step S1003 and step S1005 to step S1008 is the same as the processing illustrated in FIG. 5, any repetitive detail descriptions will be omitted.

In step S1004, the grid attachment judging unit 130 judges whether the grid is attached in radiographing or not based on the image data captured by the radiographing unit 101. If the grid 50 is attached to the radiographing apparatus 10, the processing moves to step S1005. If the grid 50 is not attached to the radiographing apparatus 10, the processing moves to step S1006.

The radiographing system (or the radiographing apparatus) according to this embodiment can judge the attachment state of the grid 50 based on image data and can select a target dose index. Because a target dose index suitable for the imaging mode can be selected without using the grid attachment detecting unit 103, an operator can appropriately evaluate a dose index.

Fourth Embodiment

A fourth embodiment will be described with reference to FIG. 2 and FIG. 9. The fourth embodiment is different from the first to third embodiments in that the selecting unit 113 selects a target dose index in accordance with the type of the grid 50.

The grid attachment detecting unit 103 illustrated in FIG. 1 is configured to detect the type of the grid 50. The grid 50 has a marker by which the type of the grid 50 can be identified. The grid attachment detecting unit 103 can read the marker to detect the type of the grid 50. The grid attachment judging unit 130 illustrated in FIG. 9 can analyze image data output from the radiographing unit 101 and detect the type of the grid 50 based on a grid pattern being a striped pattern generated by the grid 50.

The grid 50 is attached to cover the radiographing unit 101 in the radiographing apparatus 10. The grid 50 includes a plurality of metallic foils and is configured to absorb rays scattered by the subject 30 of the radiation generated by the radiation generating apparatus 10 transmitted through the subject 30.

The type of the grid 50 is predefined by a grid ratio and a grid density. The grid ratio is a ratio of the height of a metallic foil to an interval to an adjacent metallic foil. The grid ratio may be 6:1, 8:1, or 10:1, for example. The grid density is the number of metallic foils for every horizontal 1 cm. The grid density may be 40 foils/cm, 60 foils/cm, or 80 foils/cm, for example.

The grid attachment detecting unit 103 or the grid attachment judging unit 130 can detect that the grid ratio is 6:1 and the grid density is 60 foils/cm, for example, with respect to the grid 50 attached to the radiographing apparatus 10.

The selecting unit 113 is configured to select a target dose index in accordance with the type of the grid 50. For example, with a higher grid density (80 foils/cm) of the grid 50, radiation can be shielded by the grid 50. Therefore, a relatively low target dose index may be selected. With a lower grid density (40 foils/cm) of the grid 50, a relatively high target dose index may be selected.

Because the radiographing system (or the radiographing apparatus) according to this embodiment selects a target dose index suitable for the type of the grid 50, an operator can appropriately evaluate a dose index.

Fifth Embodiment

A fifth embodiment will be described with reference to FIG. 2. The fifth embodiment is different from the first to fourth embodiments in that the selecting unit 113 selects a target dose index in accordance with an image process performed in the image processing unit 117.

Having described the grid 50 is attached to the radiographing apparatus 10 in accordance with a region for imaging of the subject 30, some image processes (such as a scattered-ray component reduction process) performed in the image processing unit 117 may eliminate the necessity of attachment of the grid 50. For example, even in a case where the abdomen of the subject 30 is a region for imaging, the grid 50 may not be attached to the radiographing apparatus 10. When a scattered-ray component reduction process is performed in the image processing unit 117, it can be recognized that the grid 50 is attached to the radiographing apparatus 10. In other words, when a scattered-ray component reduction process is performed in the image processing unit 117, the selecting unit 113 selects a target dose index EIt(gridless), like a case where the grid 50 is not attached to the radiographing apparatus 10.

The radiographing system (or the radiographing apparatus) according to this embodiment can judge the attachment of the grid 50 based on an image process (scattered-ray component reduction process) in the image processing unit 117 and thus select a target dose index. Thus, without using the grid attachment detecting unit 103, a target dose index suitable for the applied imaging mode can be selected. Therefore, an operator can appropriately evaluate a dose index.

The present disclosure may be implemented by executing a program implementing one or more functions (particularly a dose index management method) of the aforementioned embodiments supplied to a radiating system or a radiating apparatus through a network or a storage medium and read by one or more processors in a computer of the radiating system or radiating apparatus. The present disclosure may also be implemented by a circuit (such as an ASIC) which implements one or more functions.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-100189 filed May 19, 2017, which hereby incorporated by reference herein in its entirety.

What is claimed is:

1. A radiographing apparatus to which a grid configured to reduce scattered rays based on radiation is attachable and configured to capture a radiation image, the radiographing apparatus comprising:
   at least one memory storing instructions; and
   at least one processor that, when executing the instructions, cause the radio graphing apparatus to:
   store a first target dose index in a case where a radiation image is captured while the grid is attached to the radiographing apparatus and a second target dose index in a case where a radiation image is captured while the grid is not attached to the radiographing apparatus for each of a plurality of image regions;
input information about an imaging region of a subject;
automatically select a target dose index for radiographing from a storage unit based on the input information about the imaging region of the subject and whether the grid is attached or not;
set a region of interest for image data based on radiation transmitted through a subject, calculate a representative pixel value in the region of interest, and acquire a dose index based on a relation between the representative pixel value and a dose of radiation;
calculate a deviation index of the dose index with respect to the target dose index; and
display, on a display, the deviation index of the dose index with respect to the target dose index,
wherein the imaging mode is an attachment state of a grid configured to shield scattered rays of the radiation,
wherein, in a case where the grid is attached to the radiographing apparatus, the first target dose index is selected, and the first target dose index and the deviation index of the dose index with respect to the first target dose index are displayed on the display,
wherein, in a case where the grid is not attached to the radiographing apparatus, the second target dose index is selected, and the second target dose index and the deviation index of the dose index with respect to the second target dose index are displayed on the display, and
wherein the first target dose index and the second target dose index are different values set in a same index standardized.

2. The radiographing apparatus according to claim 1, further comprising a storage unit configured to store a plurality of target dose indices, wherein one target dose index is selected from the plurality of target dose indices based on the imaging mode.

3. The radiographing apparatus according to claim 2, wherein the storage unit distinguishes and stores the first target dose index assuming a case where the grid is attached to the radiographing apparatus and the second target dose index assuming a case where the grid is not attached to the radiographing apparatus.

4. The radiographing apparatus according to claim 1, wherein the at least one processor further causes the radiographing apparatus to judge whether the deviation index of the dose index is within a preset allowable range or not.

5. The radiographing apparatus according to claim 4, wherein the at least one processor further causes the radiographing apparatus to generate warning information in a case where the judging unit judges that the deviation index of the dose index is not within the allowable range.

6. The radiographing apparatus according to claim 1, wherein the at least one processor further causes the radiographing apparatus to analyze the image data and judge an attachment state of the grid.

7. The radiographing apparatus according to claim 1, wherein the target dose index is selected based on the type of the grid.

8. The radiographing apparatus according to claim 1, wherein the target dose index is selected based on an image process performed on the image data in an image processing unit.

9. The radiographing apparatus according to claim 1, wherein information regarding the imaging mode is displayed on the display together with the deviation index of the dose index with respect to the target dose index.

10. A radiographing apparatus to which a grid configured to reduce scattered rays based on radiation is attachable and configured to capture a radiation, the radiographing apparatus comprising:
at least one memory storing instructions; and
at least one processor that, when executing the instructions, causes the radiographing apparatus to:
store a first target dose index in a case where a radiation image is captured while the grid is attached to the radiographing apparatus and a second target dose index in a case where a radiation image is captured while the grid is not attached to the radiographing apparatus for each of a plurality of imaging regions;
input information about an imaging region of a subject;
automatically select a target dose index for radiographing from a storage unit based on the input information about the imaging region of the subject and whether the grid is attached or not;
set a region of interest for image data based on radiation transmitted through a subject, calculate a representative pixel value in the region of interest, and acquire a dose index based on between the representative pixel value and a dose of radiation; and
display, on a display, information regarding the imaging mode, the target dose index and the dose index,
wherein the imaging mode is an attachment state of a grid configured to shield scattered rays of the radiation,
wherein, in a case where the grid is attached to the radiographing apparatus, the first target dose index is selected, and the first target dose index and the deviation index of the dose index with respect to the first target dose index are displayed on the display,
wherein, in a case where the grid is not attached to the radiographing apparatus, the second target dose index is selected, and the second target dose index and the deviation index of the dose index with respect to the second target dose index are displayed on the display, and
wherein the first target dose index and the second target dose index are different values set in a same index standardized.

11. The radiographing apparatus according to claim 10, wherein the at least one processor further causes the radiographing apparatus to operate as a judging unit configured to judge whether the dose index is within a preset allowable range or not.

12. The radiographing apparatus according to claim 11, wherein the at least one processor further causes the radiographing apparatus to operate as n information generating unit configured to generate warning information in a case where the judging unit judges that the dose index is not within the allowable range.

13. A radiographing system comprising the radiographing apparatus according to claim 1 and a radiation generating apparatus configured to generate radiation.

14. A radiographing system comprising the radiographing apparatus according to claim 10 and a radiation generating apparatus configured to generate radiation.

15. A dose index management method comprising:
storing a first target dose index in a case where a radiation image is captured while a grid is attached to a radiographing apparatus configured to capture the radiation image and a second target dose index in a case where the radiation image is captured while the grid is not attached to the radiographing apparatus;
inputting information about an imaging region of a subject;

automatically selecting a target dose index for radiographing from a storage unit based on the input information about the imaging region of the subject and whether the grid is attached or not;
setting a region of interest for image data based on radiation transmitted through a subject, calculate a representative pixel value in the region of interest, and acquiring a dose index based on a relation between the representative pixel value and a dose of radiation;
calculating a deviation index of the dose index with respect to the target dose index; and
displaying, on a display, the deviation index of the dose index with respect to the target dose index,
wherein the imaging mode is an attachment state of a grid configured to shield scattered rays of the radiation,
wherein, in a case where the grid is attached, the first target dose index is selected, and the first target dose index and the deviation index of the dose index with respect to the first target dose index, are displayed on the display,
wherein, in a case where the grid is not attached, the second target dose index is selected and the second target dose index and the deviation index of the dose index with respect to the second target dose index, are displayed on the display, and
wherein the first target dose index and the second target dose index are different values set in a same index standardized.

16. A dose index management method comprising:
storing a first target dose index in a case where a radiation image is captured while a grid is attached to a radiographing apparatus configured to capture the radiation image and a second target dose index in a case where the radiation image is captured while the grid is not attached to the radiographing apparatus;
inputting information about an imaging region of a subject;
automatically selecting a target dose index for radiographing from a storage unit based on the input information about the imaging region of the subject an whether the grid is attached or not;
set a region of interest for image data based on radiation transmitted through a subject, calculate a representative pixel value in the region of interest, and acquiring a dose index data based on a relation between the representative pixel value and a dose of; and
displaying, on a display, information regarding the imaging mode, the target dose index and the dose index,
wherein the imaging mode is an attachment state of a grid configured to shield scattered rays of the radiation,
wherein, in a case where the grid is attached, the first target dose index is selected, and the first target dose index and the deviation index of the dose index with respect to the first target dose index, are displayed on the display,
wherein, in a case where the grid is not attached, the second target dose index is selected and the second target dose index and the deviation index of the dose index with respect to the second target dose index, are displayed on the display, and
wherein the first target dose index and the second target dose index are different values set in a same index standardized.

* * * * *